(12) United States Patent
von Weymarn-Schärli et al.

(10) Patent No.: US 11,925,777 B2
(45) Date of Patent: Mar. 12, 2024

(54) TUBE ELEMENT

(71) Applicant: SoftRail Medical AG, Basel (CH)

(72) Inventors: Alexander von Weymarn-Schärli, Basel (CH); Thomas Gerig, Burgdorf (CH)

(73) Assignee: SoftRail Medical AG, Basel (CH)

( * ) Notice: Subject to any disclaimer, the term of this patent is extended or adjusted under 35 U.S.C. 154(b) by 1065 days.

(21) Appl. No.: 16/616,324

(22) PCT Filed: Jun. 1, 2018

(86) PCT No.: PCT/EP2018/064451
§ 371 (c)(1),
(2) Date: Nov. 22, 2019

(87) PCT Pub. No.: WO2018/220170
PCT Pub. Date: Dec. 6, 2018

(65) Prior Publication Data
US 2020/0086090 A1   Mar. 19, 2020

(30) Foreign Application Priority Data
Jun. 2, 2017   (EP) .................................. 17174325

(51) Int. Cl.
*A61M 25/06* (2006.01)
*A61B 1/00* (2006.01)
*A61M 25/00* (2006.01)

(52) U.S. Cl.
CPC ..... *A61M 25/0662* (2013.01); *A61B 1/00078* (2013.01); *A61M 2025/0024* (2013.01);
(Continued)

(58) Field of Classification Search
CPC .......... A61M 25/0662; A61M 25/0051; A61M 25/0043; A61M 25/0026;
(Continued)

(56) References Cited

U.S. PATENT DOCUMENTS

2011/0040282 A1*  2/2011  Uihlein ............. A61M 25/0043
604/525

FOREIGN PATENT DOCUMENTS

DE          4113265 A1    3/1992
DE    102006007974 A1    8/2007
(Continued)

OTHER PUBLICATIONS

International Search Report received in PCT/EP2018/064451, dated Aug. 9, 2018, pp. 6.
(Continued)

*Primary Examiner* — Nathan R Price
*Assistant Examiner* — Anh Bui
(74) *Attorney, Agent, or Firm* — Hard IP LLC

(57) ABSTRACT

A tube element for a device for introduction into a body passage comprises a first tube element end and a second tube element end, wherein a longitudinal dimension is formed between the first and second tube element end. The tube element has a sheath comprising an outer wall and an inner wall. A cross-sectional element is arranged between the first and second tube element ends. The cross-sectional element contains a plurality of opening arrangements. Each opening arrangement comprises a first opening containing an insert element and a second opening, the internal pressure of which can be changed by a pressure changing means.

18 Claims, 7 Drawing Sheets

(52) U.S. Cl.
CPC . *A61M 25/0051* (2013.01); *A61M 2025/0059* (2013.01); *A61M 2025/0063* (2013.01); *A61M 2025/0681* (2013.01)

(58) Field of Classification Search
CPC .. A61M 2025/0024; A61M 2025/0059; A61M 2025/0063; A61M 2025/0681; A61M 2025/0025; A61M 2025/0035; A61M 2025/004; A61B 1/00078
See application file for complete search history.

(56) References Cited

FOREIGN PATENT DOCUMENTS

| | | |
|---|---|---|
| EP | 1551490 B1 | 7/2005 |
| EP | 1917061 B1 | 5/2008 |
| WO | 2005042078 A1 | 5/2005 |
| WO | 20140143198 A1 | 9/2014 |

OTHER PUBLICATIONS

Written Opinion received in PCT/EP2018/064451, dated Aug. 9, 2018, pp. 10.

\* cited by examiner

TUBE ELEMENT

CROSS-REFERENCE TO RELATED APPLICATIONS

This application is a U.S. national stage filing under 35 U.S.C. 371 of international patent application no. PCT/EP2018/064451, filed on Jun. 1, 2018, which claims priority to European patent application no. EP17174325.5, filed on Jun. 2, 2017, the contents of both of which are incorporated herein by reference in their entirety.

TECHNICAL FIELD

The invention relates to a tube element for a device for introduction into a body passage, for example a catheter or a sluice element, which serves for introducing catheters into a body passage or a body vessel.

A variety of such sluices is known in the art. However, it has repeatedly been shown in practice that the introduction of such a sluice into a long, angular body is still a challenge for the attending physician. When such a sluice is to be laid from the groin to the head of the patient through a blood vessel, high demands are placed on the skill of the physician on the one hand and on the materials of that sluice on the other hand. This sluice has to adapt to the vessel inner wall in tight curves of the body passage, so as not to injure the vessel inner wall. The sluice must not buckle at any point, since a kink obstructs or even prevents the passage of fluids, for example rinsing fluids or medicaments.

DESCRIPTION OF RELATED ART

The Applicant has therefore disclosed in EP 1 551 490 B1 a guide device which on the one hand is sufficiently flexible and on the other hand sufficiently rigid. In EP 1 551 490 B1 it is proposed for this purpose to generate magnetic fields of different polarity along the first wire strand and along the second wire strand for selectively inducing a mutual attraction of the strands. When a magnetic field is generated, the guide device becomes rigid, when no magnetic field is generated, the guide device remains flexible, so that when inserting the guide device into the body passage, it will be sufficiently flexible, however sufficiently rigid, when providing guidance for a catheter especially in the region of a curve, for example at a branch of the vessel.

According to EP 1 551 490 B1, it is also known to stiffen a plurality of wires arranged annularly in a non-stretchable tube by means of an inflatable channel located within the annular arrangement of the wires. A disadvantage of this arrangement is the fact that the central channel is provided with (air) pressure for the stiffening of the guide device. However, the application of pressure must not hinder the introduction of the catheter in the guide device. Therefore, a sophisticated sealing system is required for such a solution.

WO2005042078 A1 shows a sluice with an elongate, outer shell body, an elongated inner body arranged in the shell body, wherein the shell body and the inner body are rotatable relative to each other by means of a control device such that the inner body at least partially rests against the shell body, or that magnetic fields of different polarity are disposed along the length of the shell body and the inner body so that shell body and inner body attract each other.

A sluice is shown in EP 1 917 061 B1, which consists of an inner tube surrounding the central lumen, an outer tube surrounding the inner tube and a sheath body which surrounds the outer tube, wherein a plurality of metal straps is arranged between the outer tube and the sheath body. The outer tube is more elastic than the inner tube. If the inner space between inner tube and outer tube is pressurized, the outer tube expands in the direction of the sheath body. As a result, the metal bands are pressed against the sheath body, which leads to a stiffening of the sluice. A similar solution is also shown in US20110040282 A1 or DE 10 2006 007974 A1.

However, the arrangement of metal bands in a sheath body of a sluice, which should have less than 5 mm outer diameter and the arrangement of an outer tube and an inner tube in a defined distance requires an intricate manufacturing technology.

An object of the invention is to develop a sluice that can be configured reversibly in a rigid or soft manner and which can be produced inexpensively by mass-production.

SUMMARY OF THE INVENTION

The solution of the objects of the invention is achieved by a device with the features of claim 1. Further advantageous embodiments of the device are subject matter of claims 2 to 20.

When the term "for example" is used in the following description, this term refers to embodiments and/or variants, which is not necessarily to be understood as a more preferred application of the teaching of the invention. Similarly, the terms "preferably," "preferred," are understood to refer to an example of a set of embodiments and/or variants, which is not necessarily to be understood as a preferred application of the teaching of the invention. Accordingly, the terms "for example," "preferably," or "preferred," may refer to a plurality of embodiments and/or variants.

The following detailed description contains various embodiments of the device according to the invention. The description of a particular device is to be considered as exemplary only. In the specification and claims, the terms "including," "comprising," "having" are interpreted as "including but not limited to."

A tube element for a device for introduction into a body passage comprises a first tube element end and a second tube element end. A longitudinal dimension is formed between the first and second tube element end. The tube element has a sheath comprising an outer wall and an inner wall. The sheath has an external diameter, wherein the longitudinal dimension amounts to at least ten times the external diameter. the first tube element end comprises a first frontal element and second tube element end comprises a second frontal element, wherein a cross-sectional element is arranged between the first tube element end and second tube element end. The cross-sectional element contains a plurality of opening arrangements, wherein the opening arrangements extend along the longitudinal dimension. Each one of the opening arrangements comprises a first opening containing an insert element and a second opening, the internal pressure of which can be changed by a pressure changing means. In particular the opening arrangements can extend from the first frontal element to the second frontal element.

The cross-sectional element can be arranged at any location of the longitudinal dimension. Each of the cross-sectional elements includes the opening arrangements, however, the size of the openings of the opening arrangements may vary at any location of the longitudinal dimension. Furthermore, the position of the opening arrangements may vary at any location of the longitudinal dimension. The openings of the opening arrangements can thus form channels. In particular, the channels formed by the openings in the direction of the longitudinal axis can be spiral-shaped, wave-shaped, helical, so that the opening arrangements are in different positions in different cross-sectional elements. According to an embodiment, the channels of the openings may extend parallel to the longitudinal axis of the tube element. The channels extend in particular from the first tube element end to the second tube element end. According to an embodiment, the channels starting at the first tube element end have a deflection in front of the second tube element end such that the pressure changing means at the first tube element end can be introduced into the channel and flow through the channel of the opening to the second tube element end or can be returned by a deflection to the first tube element end, such that a closed circuit of the pressure changing means can be realized in the tube element.

According to an embodiment, the insert element can contain at least one element of the group consisting of glass fibers, carbon fibers, wires or textile filaments. The insert element can be formed as a wire, a rope, a filament or a band. The insert element may comprise a mesh or be formed as a mesh.

According to an embodiment, an overpressure or a negative pressure can be generated in the second opening with respect to the pressure in the first opening by means of the pressure changing means. Accordingly, the pressure changing means may comprise a pressure source or a vacuum source, wherein the pressure source may contain a compressible medium. For example, an air pressure source may be provided. According to a variant, the pressure source can contain an incompressible medium. The incompressible medium may comprise a pressure fluid, in particular a pressurized liquid. Water or oil can be used as an example for a pressurized liquid.

According to an embodiment, the opening arrangement has a common wall whose wall thickness is substantially smaller than the distance of the opening arrangement from the outer wall or the inner wall of the tube element. According to an embodiment, the wall thickness of the common wall can be less than half the distance of the opening arrangement from the outer wall or the inner wall of the tube element. According to an embodiment, the wall thickness of the common wall can be less than one third of the distance of the opening arrangement from the outer wall or the inner wall of the tube element. According to an embodiment, the wall thickness of the common wall can be less than a quarter of the distance of the opening arrangement from the outer wall or the inner wall of the tube element.

According to an embodiment, the wall thickness of the common wall can be less than one fifth of the distance of the opening arrangement from the outer wall or the inner wall of the tube element. According to an embodiment, the wall thickness of the common wall can be less than one tenth of the distance of the opening arrangement from the outer wall or the inner wall of the tube element. A pressure change in the opening arrangement thus has predominantly, in particular exclusively, an effect on the first and second openings, but not on an outer or inner wall. The intermediate wall can be displaced by a change in the internal pressure such that the insert element in the first opening is selectively blockable or detachable. The intermediate wall is thus deformable due to the small wall thickness such that it can be moved from the original position in the direction of the insert element until the insert element rests on the intermediate wall or another wall of the opening. By the movement of the intermediate wall, the opening is deformed such that the insert element is clamped in the opening.

The blocking of the insert element causes an increase in the friction between the insert element and the inner wall of the first opening, whereby a stiffening of the tube element is effected. The release of the insert element from the inner wall of the first opening causes a reduction of the frictional forces acting on the inner wall, so that the flexibility of the tube element is increased. In particular, the insert element is bendable, wherein buckling of the tube element is prevented at any location between the first tube element end and the second tube element end.

According to an embodiment, the tube element contains at least three opening arrangements. The use of three or more opening arrangements makes it possible to achieve a stiffening of the tube element even with a small number of opening arrangements. If three opening arrangements are provided, a good stability of the tube element is ensured.

In particular, the opening can have a cross section which comprises an element from the group consisting of circular, elliptical, arcuate, C-shaped, slot-like, crescent-shaped, dumbbell-shaped cross-sections.

Each of the openings has an opening center, wherein the opening center is formed by the centroid of the opening. According to an embodiment, the opening centers of an opening arrangement are arranged substantially on a common circumferential line of the tube element. In particular, the circumferential line of the tube element may be arranged at a distance from the outer wall and the inner wall. The distance may correspond, in particular, to the central distance measured along a central axis between the outer wall and the inner wall, wherein the distance deviates by a maximum of 25% from the central distance.

The arrangement of the opening arrangements in an annular region, which runs centrally between the outer wall and the inner wall, can ensure that the pressure changes in the opening arrangements at most have an insignificant effect on the outer wall or the inner wall of the tube element. If the outer wall rests in the body against the inner wall of a vessel, it can be ensured by this configuration that no irritation of the inner wall of the vessel may result from the pressure fluctuations that could lead to bulging of the tube element, which in turn may result in an unacceptable pressure on the inner wall of the vessel.

The opening center points of an opening arrangement can be arranged essentially on a common diameter line of the tube element. For example, the opening center of the first opening may have a smaller radial distance from the center axis than the opening center of the second opening.

According to an embodiment, the insert element can be arranged eccentrically in the first opening. According to a further embodiment, the second opening can at least partially enclose the first opening. When the second opening is subjected to an overpressure, the intermediate wall is pressed over a larger surface on the first opening, so that the frictional forces acting on the insert element can be increased by this arrangement.

According to an embodiment, the opening arrangement may comprise more than two openings. For example, the first opening containing the insert element may be surrounded by two or more openings that are individually or jointly subjected to a pressure change. This variant makes it possible to control the rigidity of the tube element by selecting a selection of different stages ranging from a rigid tube element to a floppy tube element by subjecting only one of the openings to a pressure change, or subjecting two or more openings to a pressure change simultaneously.

According to an embodiment, the tube element consists of a plurality of tube element portions. The tube element portions can have a coaxial arrangement. The tube element portions have a common longitudinal axis, which coincides with the longitudinal axis of the tube element by definition. The tube element portions are thus nested tubes. In other words, the sum of the tube element portions results in the tube element. The tube element portion can serve to facilitate or enable the conveyance of solid, liquid or gaseous substances or of components, for example measuring devices, through the lumen formed by the inner wall. Such a tube element portion may, for example, comprise a coating which, for example, acts as a diffusion barrier. A tube element portion may be formed so as to serve the additional stiffening of the inner wall so that any kinking can be avoided when the tube element has to be passed through curved body passages. A plurality of coaxially arranged nested tube element portions can also be provided to fulfill this function.

According to an embodiment, the tube element portion has at least one recess which is arranged in the sheath. The recess is characterized in that the wall thickness of the tube element portion in the region of the recess is smaller than the wall thickness of the sheath. In particular, the wall thickness of the tube element portion can be zero in the region of the recess. The recess may in particular comprise a groove.

According to an embodiment, the tube element portion may have a slotted sheath. The slotted sheath may in particular have a radial slot. Several radial slots can be arranged parallel to each other. Such a slot may extend over at least one third of the circumference of the sheath. According to an embodiment, a tube element portion may be provided which has a sheath which contains a helical slot.

The tube element portion can have a plurality of recesses, in particular slots, the ends of which are formed offset from one another on the lateral circumference of the sheath. The slots may have a maximum slot width of one millimeter and may extend over a portion of the sheath.

According to an embodiment, the recesses may be formed as helical cuts. Each of these slot arrangements ensures high torsional rigidity while maintaining good flexibility, thereby providing a higher radial displacement capacity compared to conventional thin walled tubes.

The flexibility also prevents the formation of kinking, since the inner body can not provide any significant resistance to bending, since the slots cause a widening on the tension side and a constriction on the pressure side of the tube element portion. Angular displacements, axial displacements or combinations of all three types of displacement are thus effectively compensated by the flexible tube element portion.

Such a slotted tube element portion can be used in particular for applications in which lower forces are to be transmitted. The tube element portion has a high torque capacity despite a displacement compensation. Especially with devices that have to be moved back and forth in a channel and for which a repeatable positioning accuracy plays an important role, there are advantages in the application with respect to the torsional rigidity and freedom of rotation of the slotted tube element portion.

The slotted tube element portion is therefore suitable for precision applications with filigree components such as catheters or sluices. High radial lateral forces could, for example, affect or injure the vessel walls.

According to an embodiment, the outer diameter of the tube element is in the range of 1 to 10 mm inclusive. According to an embodiment, the outer diameter of the tube element is in particular 3.3 mm. The inner diameter of the tube element which forms a lumen can be in the range of 0.5 to 2.5 mm.

According to an embodiment, the tube element has a sheath which forms a cross-sectional element comprising an outer wall and an inner wall. The sheath has an outer diameter, wherein the longitudinal dimension of the tube element corresponds to at least ten times the outer diameter. The inner diameter of the sheath corresponds to the outer diameter of an annular opening adjacent to the inner wall of the sheath. The second opening is thus formed as an annular opening in cross section. The cross section is arranged in normal direction with respect to the longitudinal axis of the tube element.

An inner tube is arranged inside the opening, which contains for example a plastic or consists of plastic. The outer diameter of the inner tube corresponds to the inner diameter of the opening. Advantageously, the inner tube is arranged concentrically with respect to the sheath.

The inner tube can include a stiffening element or a stiffening element may be mounted on the inside of the inner tube. The stiffening element can be configured as a spirally arranged wire element or band element. The stiffening element can also be designed as a mesh. If no stiffening element is provided or the stiffening element is arranged in the interior of the inner tube, a central cavity or lumen is located inside the stiffening element and/or the inner tube. The stiffening element can be laminated, for example, in the inner tube. The stiffening element can be located between the central cavity and the inner tube or it can be located between the inner tube and the cross-sectional element.

The tube element portion surrounding the central cavity, that is to say in particular the inner tube or the stiffening element, can be provided with a coating according to each of the exemplary embodiments so that a fluid located in the central cavity, in particular a liquid, does not interact with the inner tube or the stiffening element.

The cross-sectional element can include a plurality of opening arrangements. The opening arrangements extend in the direction of the longitudinal dimension from the first frontal element to the second frontal element or from the first tube element end to the second tube element end. According to an exemplary embodiment, each opening arrangement comprises a first opening each containing an insert element and a second opening whose internal pressure can be changed by a pressure changing means. By means of the pressure changing means, an overpressure or a negative pressure in the second opening can be generated relative to the internal pressure in the first opening.

According to an embodiment, each of the first openings containing an insert element includes an associated second opening. The tube element contains at least three opening arrangements according to this embodiment. The first openings can be connected to the corresponding second openings via a channel or a constriction. Optionally, a partition may be provided. The partition may be formed as a film or a membrane.

The opening walls can be displaced by changing the internal pressure in each one of the first or second openings so that the insert element in the first opening is selectively blocked or detachable. In particular, one of the first or second openings can be evacuated so that the opening walls come into contact with the insert element. Alternatively, one of the first or second openings can be subjected to an overpressure, whereby the position of the insert element in the associated opening can be fixed.

According to an embodiment, the tube element can be formed as a composite element containing at least two different materials. In particular, the composite element may contain a first plastic and at least one element selected from the group consisting of plastics or metallic materials. In particular, the sheath and/or one of the tube element portions may be formed as a composite element.

The tube element according to one of the preceding embodiments can include the second opening which is configured as an annular opening in cross-section.

A tube element portion is positioned next to the inner wall of the sheath of a tube element according to one of the preceding embodiments, which is configured as an inner tube or as a stiffening element. The inner tube according to one of the preceding embodiments can contain a plastic or consist of a plastic.

The inner tube according to one of the preceding embodiments can include a stiffening element or a stiffening element may be mounted on the inside of the inner tube. The stiffening element according to one of the preceding embodiments can be formed as a spirally arranged wire element or as a band element or as a mesh.

The tube element according to one of the preceding embodiments can include a central cavity for receiving a fluid. The outer wall of the cavity may be formed by the inner wall of the sheath or one of the tube element portions.

The outer wall of the cavity can be formed by the inner wall of the inner tube or the stiffening element according to one of the preceding embodiments. The inner wall of the sheath, one of the tube element portions or of the inner tube or of the stiffening element can contain a coating according to one of the preceding embodiments. The coating can in particular be configured as a fluid-tight coating.

A method for producing a tube element according to one of the preceding embodiments comprises a step of the common extrusion of the tube element body, the opening arrangements and the insert elements.

The tube element can contain at least one element of the group of thermoplastic polymers. For example, the plastic can contain polypropylene or polyamide or consist of at least one of the plastics selected from the group of polypropylenes or polyamides.

Examples of other suitable thermoplastic polymers are polyethylene (PE), polymethylpentene (PMP) polypropylene (PP), polystyrene (PS), acrylonitrile butadiene styrene (ABS), polyamides (PA) in general, polyamide 6 (PA 6), polyamide 6,6 (PA 66), polyamide 11 (PA 11), polyamide 12 (PA 12), polyamide 61 (PA610), polycarbonate (PC), polyvinyl chloride (PVC), polyethylene terephthalate (PET), polyethylene terephthalate glycol (PETG), cellulose acetate butyrate (CAB), polyether ether ketone (PEEK), polyacrylonitrile (PAN), polyamideimide (PAI), polybutylene terephthalate (PBT), polyurethane (PU), thermoplastic polyurethane (TPU), polyester (PES), polyvinyl alcohol (PVA), polyphenylene oxide (PPO), polymethylmethacrylate (PMMA), polysulfone (PSU), polyphenylene sulfide (PPS), polyphenylene sulfone (PPSU), polyethersulfone (PES), polyetherimide (PEI), perfluoroalkoxyalkane (PFA), polychlorotrifluoroethylene (PCTFE), polyvinylidene fluoride (PVDF), polyphthalimide (PPA), styrene-butadiene (SB), acrylic styrene acrylic ester (ASA), ethylene vinyl acetate copolymer (EVA), polyaryletherketone (PAEK), ethylene-butyl acrylate copolymer (EBA), polyoxymethylene (POM), polybutadiene (PBD), polyisoprene (PIP), polychloroprene and/or polyalkyl vinyl ether, polylactides (PLA), acrylonitrile butadiene styrene (ABS), styrene acrylonitrile (SAN), polycarbonate (PC), polyoxymethylene (POM), polysulfone (PSU), polyphenylene sulfide (PPS), perfluoroalkoxyalkane (PFA), polyvinylidene fluoride (PVDF), polymethyl methacrylate (PMMA), and/or thermoplastic elastomers.

Further examples of elastomers are, for example, block copolymers of a macromolecule based on styrene polymers (TPE-S), polyetheramides (TPE-A), polyether esters (TPE-E), thermoplastic polyurethanes (TPE-U) and—on the other hand—elastomer blends which coexist as a thermoplastic, uncrosslinked and a partially and/or fully crosslinked phase, for example thermoplastic elastomers based on polyolefin blends (TPE-V).

In addition, all conceivable blends or copolymers of different thermoplastics can be used.

A device according to the present invention has especially the advantages listed below over the known solutions. The device can be manufactured continuously by means of an extrusion process. In particular, a plurality of tubular layers can be produced simultaneously, wherein in particular a sheath body with a plurality of channels can be produced and wherein the channels can consist of different materials.

BRIEF DESCRIPTION OF THE DRAWINGS

The device according to the invention will now be illustrated with reference to some embodiments. It is shown in FIG. 1 a radial section through a first exemplary embodiment of a tube element according to the invention, FIG. 2 a radial section through a second exemplary embodiment of a tube element according to the invention, FIG. 3 a radial section through a third exemplary embodiment of a tube element according to the invention, FIG. 4 a radial section through a fourth exemplary embodiment of a tube element according to the invention, FIG. 5 a radial section through a fifth exemplary embodiment of a tube element according to the invention, FIG. 6 a radial section through a sixth exemplary embodiment of a tube element according to the invention, FIG. 7 a radial section through a seventh exemplary embodiment of a tube element according to the invention, FIG. 8 an example for the use of a tube element according to one of the embodiments, FIG. 9 a detail of a device for introducing a tube element into a body passage, FIG. 10 a longitudinal section through an eighth embodiment of a tube element according to the invention, FIG. 11 a longitudinal section and a radial section through a ninth embodiment of a tube element according to the invention, FIG. 12 a longitudinal section of an exemplary embodiment of a tube element portion according to the invention, FIG. 13 a radial section of the exemplary embodiment of a tube element portion according to the invention, FIG. 14 a radial section through an eighth embodiment of a tube element according to the invention, FIG. 15 a radial section through a ninth embodiment of a tube element according to the invention.

DETAILED DESCRIPTION

Figure 1:
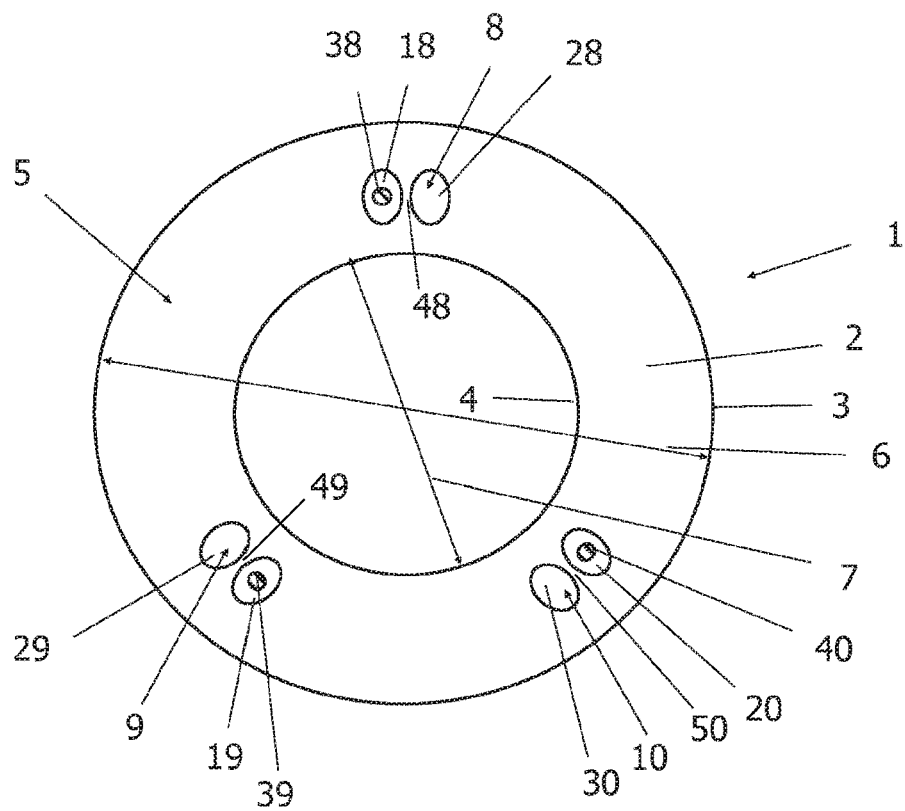
Figure 10:
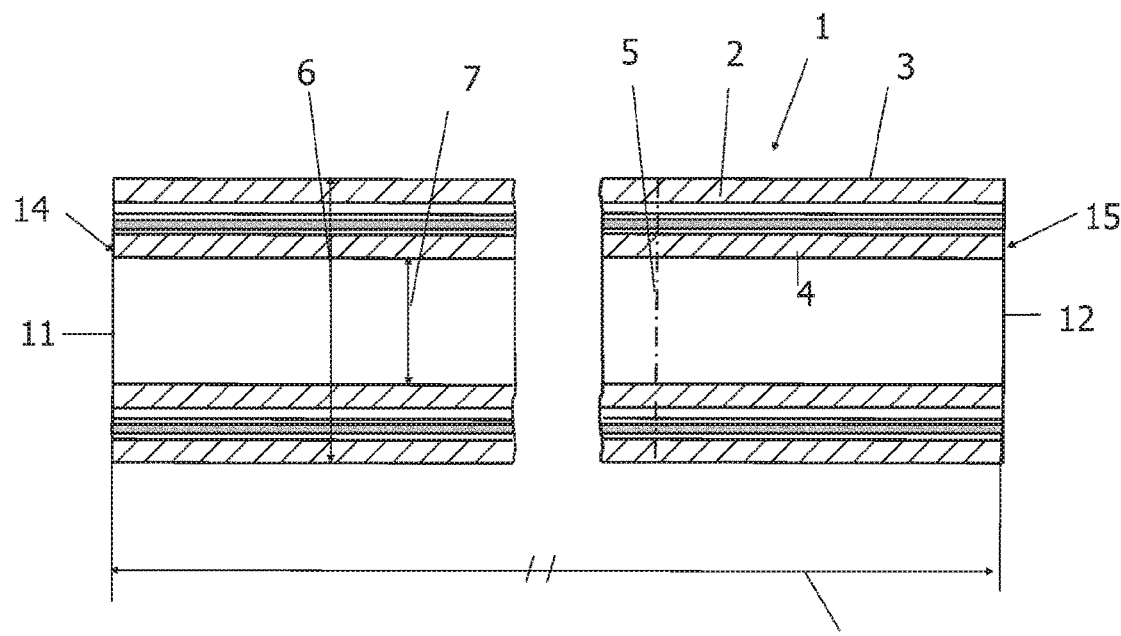

FIG. 1 shows a tube element 1 for a device 100 for insertion into a body passage, the tube element 1 having a first tube element end 11 and a second tube element end 12, which is shown in FIG. 10. In FIG. 1, no hatchings have been made in order to increase the clarity of the representation. FIG. 1 shows a cross-sectional element 5 in a radial section normal to the longitudinal axis. A longitudinal dimension 13 is formed between the first and second tube element ends 11, 12, which coincides with the longitudinal axis when the tube element 1 has a rotationally symmetrical shape. The tube element has a sheath 2 which comprises an outer wall 3 and an inner wall 4. The sheath 2 has an outer diameter 6, wherein the longitudinal dimension 13 is at least ten times the outer diameter 6. The first tube element end 11, has a first frontal element 14 and the second tube element end 12 has a second frontal element 15 according to FIG. 10. A cross-sectional element 5 is arranged between the first frontal element 14 and the second frontal element 15. The cross-sectional element 5 may be located at any position between the first tube element end 11 and the second tube element end 12.

The cross-sectional element 5 contains a plurality of opening arrangements 8, 9, 10. The opening arrangements 8, 9, 10 extend in the direction of the longitudinal dimension 13 from the first frontal element 14 to the second frontal element 15 and from the first tube element end 11 to the second tube element end 12. Each of the opening arrangements 8, 9, 10 comprises a first opening 18, 19, 20 containing an insert element 38, 39, 40 and a second opening 28, 29, 30 whose internal pressure is adjustable by a pressure changing means. An overpressure or a negative pressure can be generated in the second opening 28, 29, 30 relative to the internal pressure in the first opening 18, 19, 20 by means of the pressure changing means. The tube element 1 contains three opening arrangements 8, 9, 10.

Each of the opening arrangements 8, 9, 10 has an intermediate wall 48, 49, 50, whose wall thickness is substantially smaller than the distance of the opening arrangement 8, 9, 10 from the outer wall 3 or the inner wall 4.

The intermediate wall 48, 49, 50 is displaceable by changing the internal pressure of one of the first or second openings 18, 19, 20, 28, 29, 30 such that the insert element 38, 39, 40 in the first opening 18, 19, 20 optionally blockable or detachable.

Figure 2:
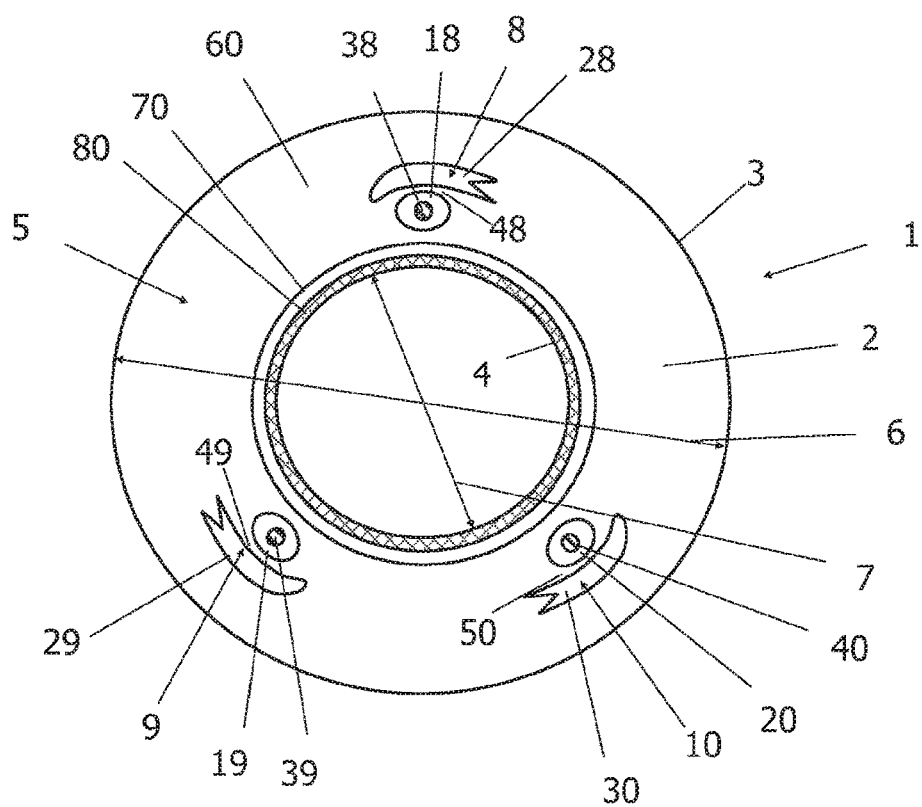

FIG. 2 shows a radial section through a second exemplary embodiment of a tube element 1 according to the invention. The tube element according to FIG. 2 differs from the tube element according to FIG. 1 in that it consists of a plurality of tube element portions 60, 70, 80. The opening arrangements 8, 9, 10 have a different arrangement from the arrangement according to FIG. 1. Although three opening arrangements 8, 9, 10 are provided as in FIG. 1, the first openings 18, 19, 20 are not arranged adjacently to the respective second openings 28, 29, 30. The opening center of the first openings is closer to the longitudinal axis than the opening center of the second openings 28, 29, 30. The second openings 28, 29, 30 have the shape of a curved elongated hole here. The concavely curved side of the second openings 28, 29, 30 faces the first openings 18, 19, 20, the convexly curved side of the second openings 28, 29, 30 is arranged substantially opposite to the concavely curved side of the second openings 28, 29, 30 and averted from the first openings 18, 19, 20.

Figure 3:
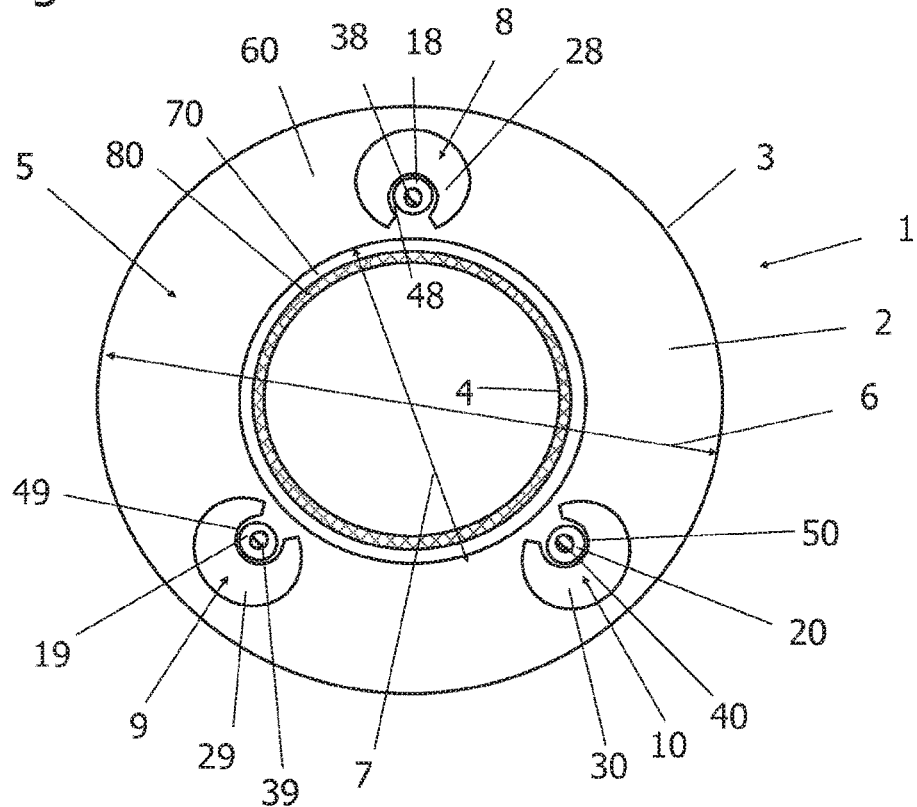

FIG. 3 shows a radial section through a third exemplary embodiment of a tube element 1 according to the invention. The tube element according to FIG. 3 differs from the tube element according to FIG. 1 in that it consists of a plurality of tube element portions 60, 70, 80. The opening arrangements 8, 9, 10 have a different arrangement from the arrangement according to FIG. 1 or FIG. 2. Although three opening arrangements 8, 9, 10 are provided as in FIGS. 1 and 2, the first openings 18, 19, 20 are located substantially within the associated second openings 28, 29, 30. The opening center of the first openings is closer to the longitudinal axis than the opening center of the second openings 28, 29, 30 according to this embodiment. The second openings 28, 29, 30 have the shape of a C according to this embodiment. The inner area, that is the area between the legs of the C-shape of second openings 28, 29, 30 includes the first openings 18, 19, 20 at least partially and the insert element 38, 39, 40 which is located in the first openings 18, 19, 20. The legs of the C-shape are open in the direction of longitudinal axis according to this embodiment. As the second openings 28, 29, 30 almost completely enclose the first openings 18, 19, 20, compressive forces can act on almost the entire circumference of the insert element 38, 39, 40. Therefore, in this case, the frictional forces can act on almost the entire circumference of the insert element 38, 39, 40.

Figure 4:
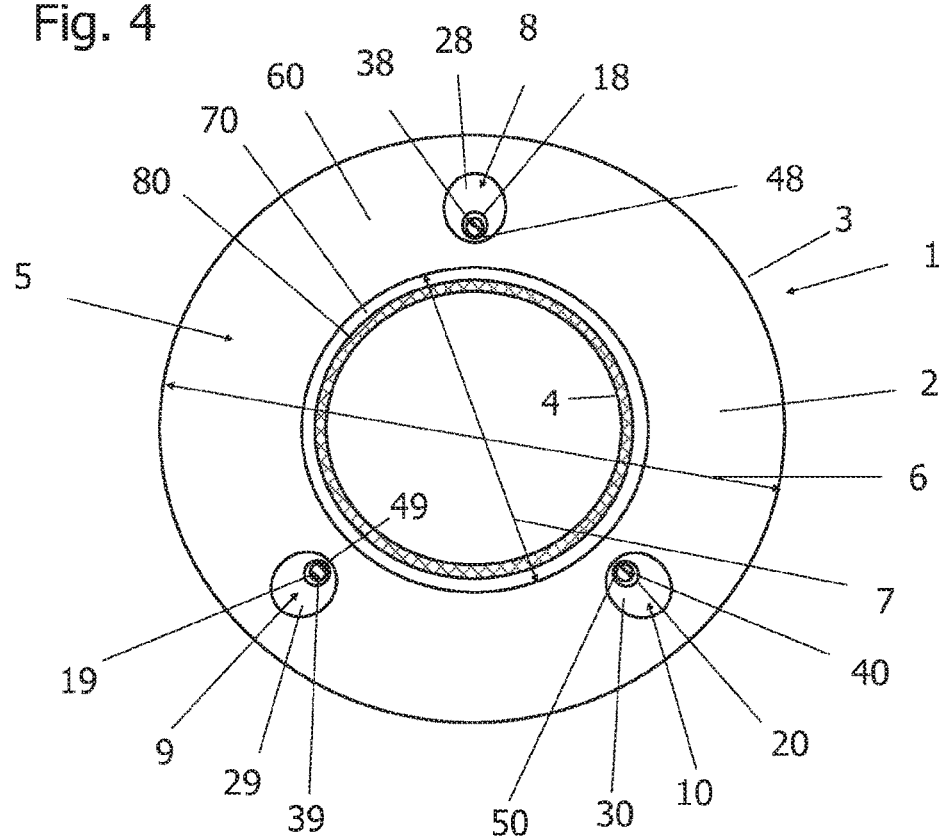

FIG. 4 shows a radial section through a fourth exemplary embodiment of a tube element according to the invention. The tube element 1 according to FIG. 4 differs from the tube element according to FIG. 1 in that it consists of a plurality of tube element portions 60, 70, 80. Although three opening arrangements 8, 9, 10 are provided as in the preceding embodiments, the first openings 18, 19, 20 are located completely within the associated second openings 28, 29, 30. The opening center of the first openings is positioned closer to the longitudinal axis than the opening center of the second openings 28, 29, 30 in this embodiment. Here, the second openings 28, 29, 30 have the shape of an ellipse.

The second openings 28, 29, 30 thus contain the first openings 18, 19, 20, wherein the first openings are separated from the second openings by a common intermediate wall 48, 49, 50, the common intermediate wall representing the outer boundary of the first openings 18, 19, 20. As the second openings 28, 29, 30 completely enclose the first openings 18, 19, 20, compressive forces can act on the entire circumference of the insert element 38, 39, 40. Therefore, in this case, the frictional forces can act on the entire circumference of the insert element, so that a maximum stiffening effect is achievable.

Figure 5:
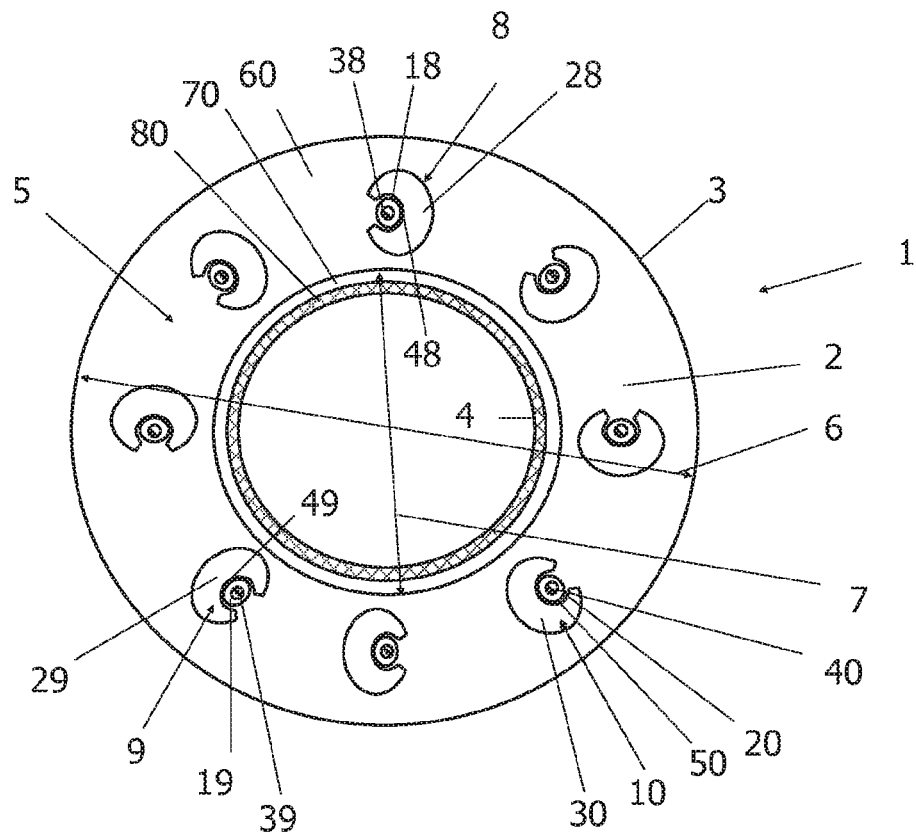

FIG. 5 shows a radial section through a fifth exemplary embodiment of a tube element 1 according to the invention. The tube element according to FIG. 5 differs from the tube element according to FIG. 3 in that the first openings 18, 19, 20 are essentially located within the associated second openings 28, 29, 30 and the opening center of the first openings 18, 19, 20 in this embodiment has substantially the same normal distance from the longitudinal axis as the opening center of the second openings 28, 29, 30. The second openings 28, 29, 30 have the shape of a C is similar to FIG. 3, but the C is rotated by an angle of substantially 90 degrees with respect to the arrangement of FIG. 3. The inner region, that is to say the region between the legs of the C-shape of the second openings 28, 29, 30, contains the first openings 18, 19, 20 at least partially and the insert element 38, 39, 40 located in the first openings 18, 19, 20. According to this embodiment, the legs of the C-shape are open in the direction of the common circumference, the circumference being formed by a circle which contains the opening centers of the first and second openings. As the second openings 28, 29, 30 almost completely enclose the first openings 18, 19, 20, compressive forces can act on almost the entire circumference of the insert element 38, 39, 40. Therefore, in this case, the frictional forces can act on almost the entire circumference of the insert element.

In FIG. 5, eight opening arrangements are provided instead of three opening arrangements, wherein only three of the opening arrangements are designated. The number of opening arrangements can be chosen arbitrarily, but it is advantageous for stability reasons, if at least three opening arrangements are provided.

Figure 6:
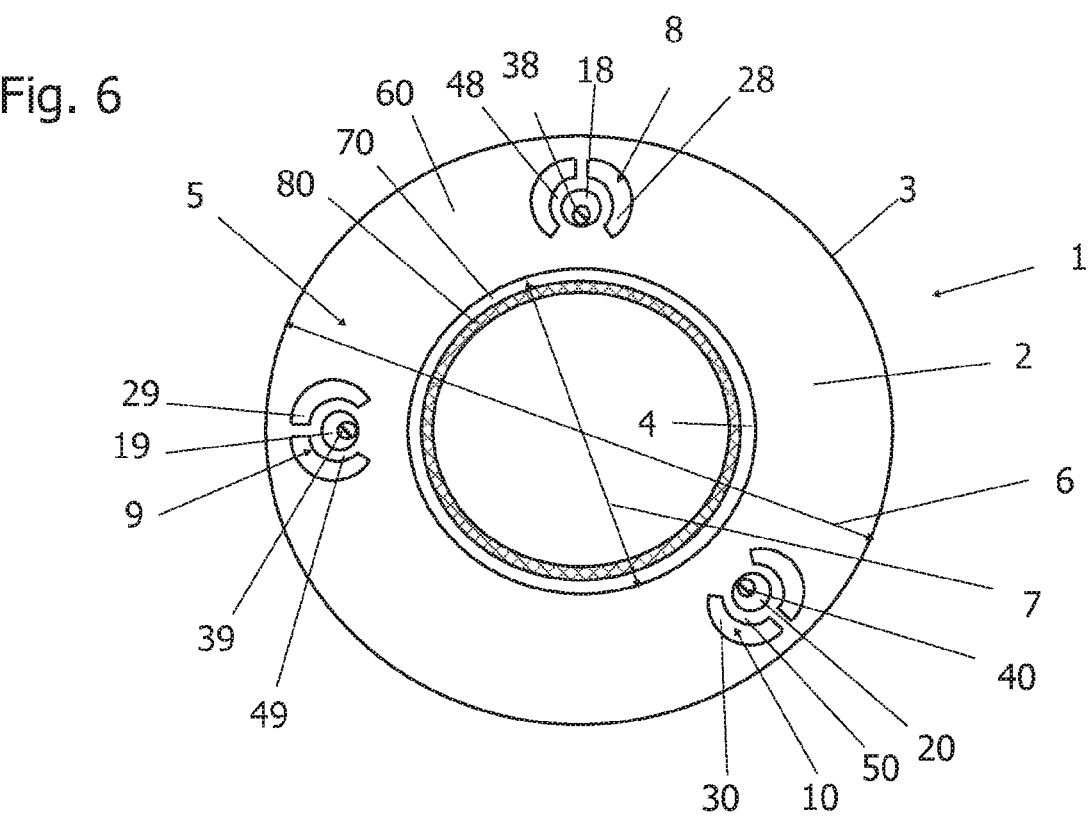

FIG. 6 shows a radial section through a sixth exemplary embodiment of a tube element according to the invention. The tube element according to FIG. 6 differs from the tube element according to FIG. 3 in that the opening arrangements 8, 9, 10 have first openings which essentially are arranged within the associated second openings 28, 29, 30, but each of the second openings 29, 29, 30 consists of two partial openings. The opening center of the first openings in this embodiment is closer to the longitudinal axis than the opening center of the second openings 28, 29, 30, wherein both partial openings are added together to determine the opening center. The partial openings may have cross sections which are arranged mirror-symmetrically to each other.

The cross-sectional areas of the partial openings which belong to an opening arrangement can in particular be substantially of the same size. Here, the second openings 28, 29, 30 have the shape of a C which is segmented along its plane of symmetry. The inner area, that is to say the area between the legs of the segmented C-shape of the second openings 28, 29, 30 contains the first openings 18, 19, 20 at least partially and the insert element 38, 39, 40, which is located in the first openings 18, 19, 20. The legs of the C-shape extend according to this embodiment in the direction of the longitudinal axis and are open in the direction of the outer wall 3. As the partial openings of the second openings 28, 29, 30 almost completely surround the first openings 18, 19, 20, compressive forces can act on almost the entire circumference of the insert element 38, 39, 40. Therefore, in this case, the frictional forces can act on almost the entire circumference of the insert element. In addition, means can be provided to adjust the pressure in each of the partial openings. Therefore, according to this embodiment, improved adjustment options are available in order to obtain a pressure-dependent adjustable stiffness of the tube element 1.

Figure 7:
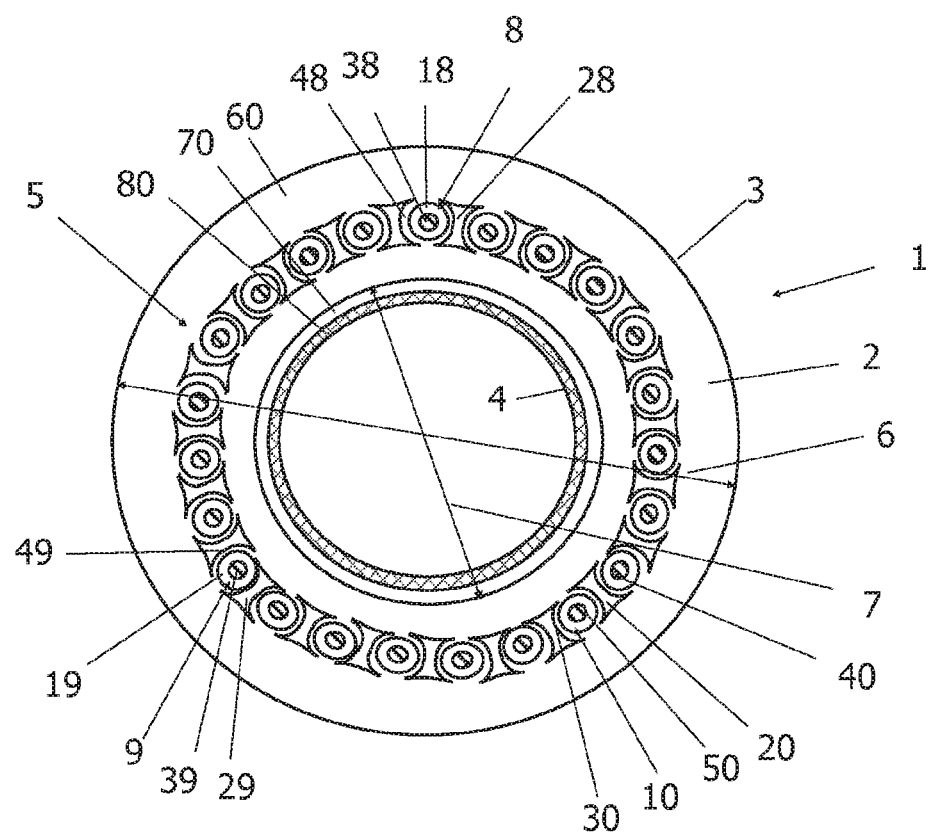

FIG. 7 shows a radial section through a seventh exemplary embodiment of a tube element 1 according to the invention. The tube element according to FIG. 7 differs from the tube elements of the preceding embodiments in that a multiplicity of opening arrangements 8, 9, 10 is arranged in an annular manner in the sheath 2 of the tube element 1 or of the tube element portion 60. Arbitrarily, three of the opening arrangements have been designated, whereby identical elements bear the same reference numerals. The opening arrangements have first openings 18, 19, 20, which essentially adjoin the associated second openings 28, 29, 30.

This results in a chain-like structure of the opening arrangements, because the second opening always adjoins an adjacent opening arrangement, here illustrated exemplarily by the openings 28, 29, 30, and thus a pressure action affects all the first openings 18, 19, 20 uniformly and quickly. Again, only three openings are exemplary picked out of these first openings 18, 19, 20 in order not to overload the graphical representation. The opening center of the first openings 18, 19, 20 is positioned in this embodiment at the same radial distance from the longitudinal axis as the opening center of the second openings 28, 29, 30, which are configured as substantially dumbbell-shaped openings. According to this embodiment, a particularly fast change between states of different stiffness is possible.

Figure 8:
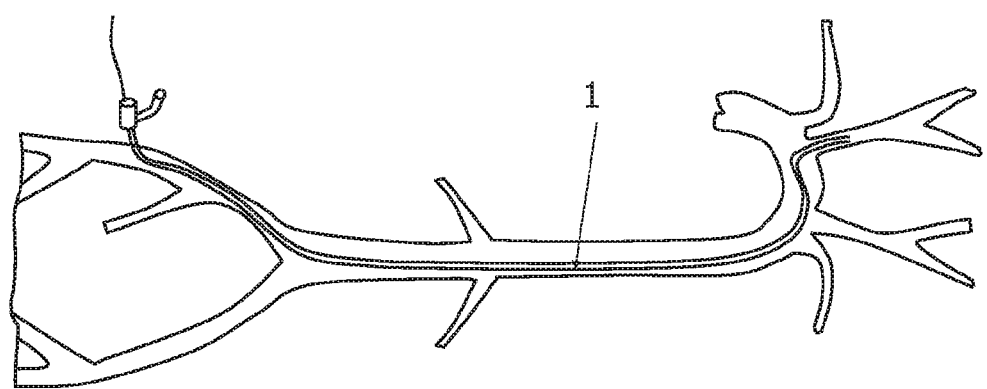

FIG. 8 shows a use example of a tube element 1 according to one of the embodiments, wherein the device is used as a sluice, which is partially inserted in a body passage. The tube element 1 can also be used in a catheter. The body passage may be formed as part of a vessel, for example comprising an artery or vein. The sluice allows access to the body while avoiding high blood loss. The vessels vary between different patients and age groups. Therefore, a sufficient flexibility is required for the device to follow all the bends of the vessel and sufficient rigidity to be able to insert the device kink-free in the vessel. The displacement path can sometimes amount to 50 cm or more when a device must be guided from the groin to the head of the patient.

Figure 9:
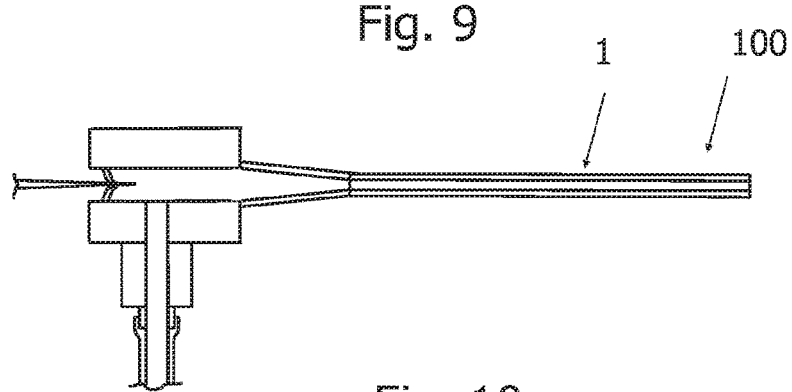

FIG. 9 shows a detail of a sluice into which a dilator can be inserted to position the sluice in a body passage. The vessel-side end of the sluice can be formed for example by a tube element according to one of the preceding embodiments. A haemostatic valve and a side port are provided at the user end of the sluice is analogous to the prior art. The side port contains a channel that can be used, for example, to supply a rinse fluid to flush the lumen of the tube element. A dilator can be inserted into the lumen so that the tube element receives additional stiffening when it has to be inserted through the vessel wall into the vessel. The sluice can contain a guide wire, which can also be guided in the lumen.

Figure 11:
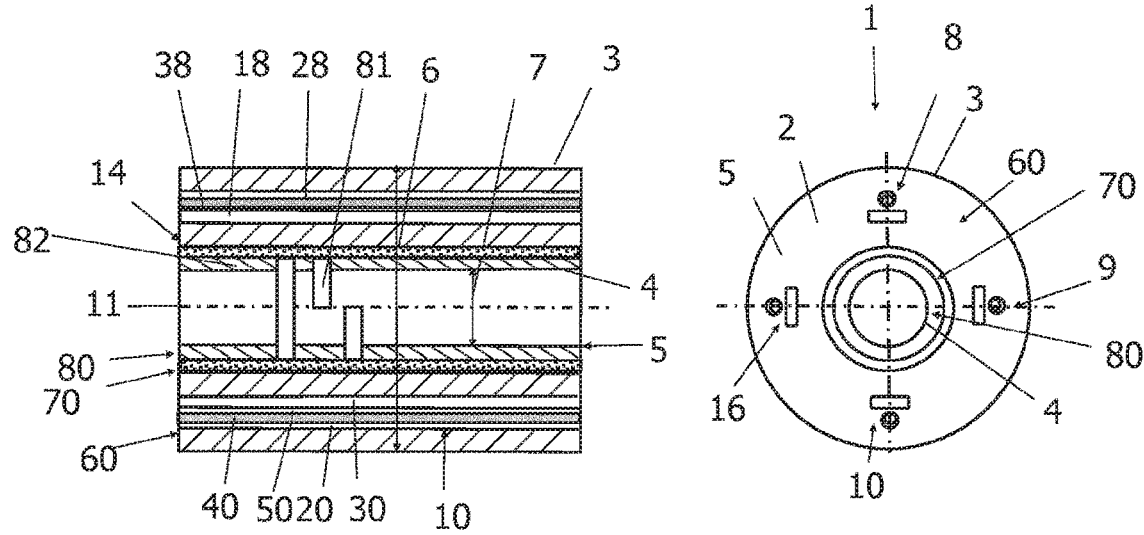

FIG. 10 shows a further exemplary embodiment of a tube element 1. The tube element 1 according to FIG. 10 is shown in longitudinal section. The longitudinal section shows only a part of the tube element 1, a part of the tube element 1 has been omitted in order to better illustrate the structure of the tube element 1. The tube element 1 corresponds to the arrangement according to FIG. 1, with the difference that an opening arrangement 8 is shown cut in the upper half of the drawing and an opening arrangement 10 is shown cut in the lower half of the drawing. FIG. 10 shows the course of the longitudinal dimension 13, which corresponds to the longitudinal axis. The tube element 1 extends from the first tube element end 11 to the second tube element end 12. The first tube element end 11 has a first frontal element 14. The second tube element end 12 has a second frontal element 15. The sheath 2 of the tube element 1 extends in each case from the outer wall 3 to the inner wall 4. FIG. 11 also shows the outer diameter 6 and the inner diameter 7 of the tube element. The inner wall 4 bounds a cavity or lumen in which, for example, a dilator, as shown in FIG. 9, can be introduced.

FIG. 11 shows a further exemplary embodiment of a tube element 1. The tube element 1 according to FIG. 11 is shown both in longitudinal section and as a radial section. The longitudinal section shows only a part of the tube element 1, namely the part up to the cross-sectional element 5, shown here as a sectional area, which is part of the tube element portion 60. The tube element portion 60 has a sheath 2 which comprises an outer wall 3 and an inner wall 4. The sheath 2 has an outer diameter 6, wherein the longitudinal dimension 13 is at least ten times the outer diameter 6. The right-hand part of FIG. 11 therefore shows the plan view of the cross-sectional element 5. According to FIG. 11, four opening arrangements 8, 9, 10, 16 are provided.

The tube element according to FIG. 11 differs from the tube elements according to one of FIGS. 2 to 8 in that it consists of a plurality of tube element portions 60, 70, 80, wherein the tube element portion 80 has at least one recess 81 in the sheath 82. The wall thickness of the tube element portion 80 is smaller in the region of the recess 81 than the wall thickness of the sheath 82. The recess 81 is configured as a slot according to FIG. 11. In FIG. 11, three radial slots are visible. These slots may comprise different segments of the sheath 82, so that a deflection of the tube element 1 of the longitudinal dimension 13 in any direction in space is possible.

Figure 12:
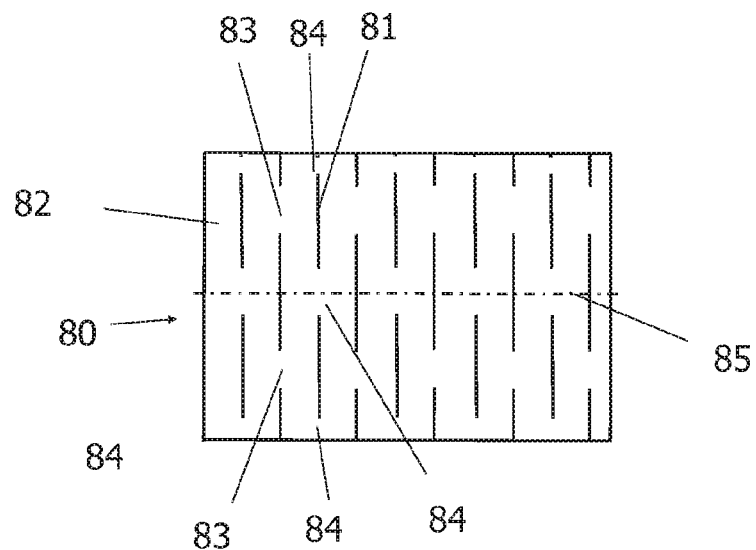

FIG. 12 shows an embodiment of a tube element portion 80. The tube element portion 80 contains a plurality of recesses 81 in the sheath 82. The recesses 81 are formed as slots. The slots have a slot width of a maximum of 1 mm. The slots are shown in simplified form as vertical lines. The slots extend over part of the sheath periphery.

According to the present embodiment, the slots have an inclination angle of approximately 90 degrees with respect to the longitudinal axis 85 of the tube element portion 80. The slots can include an inclination angle of less than 90 degrees with the longitudinal axis 85. According to this embodiment, not shown in the drawings, the slots form partial sections of a spiral. Adjacent slots can be arranged offset to one another. The slots, which extend in a cross-sectional area, may comprise a proportion of 10 up to and including 90% of the sheath circumference according to this embodiment. In particular, the slots can comprise a proportion of 20% up to and including 75% of the sheath circumference.

Each of the slot segments of a cross-sectional area is interrupted by a connecting element 83 and each of the slot segments of an adjacent cross-sectional area is interrupted by a connecting element 84. In particular, a plurality of connecting elements 83, 84 may be provided for each cross-sectional area. The connecting elements of a first slot in a first cross-sectional area are designated by reference numeral 83. The connecting elements of an adjacent slot in a second cross-sectional area are designated by reference numeral 84. The segment length of the connecting elements 83, 84 as well as the segment length of the slots extending between the connecting elements 83, 84 may differ in each cross-sectional area. The segment length of the connecting elements 83, 84 as well as the segment length of the slots extending between the connecting elements may differ in each adjacent cross-sectional area.

Figure 13:
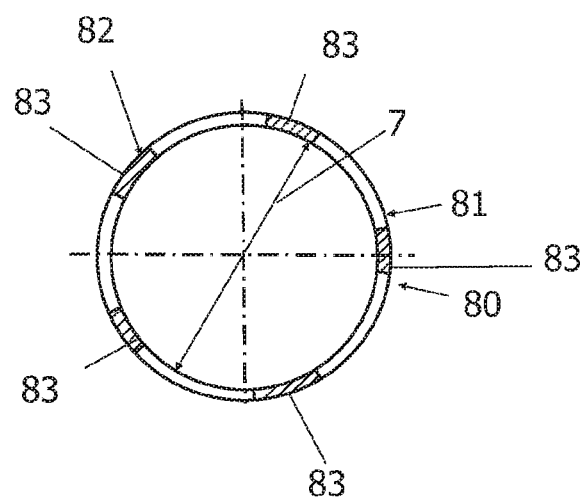

FIG. 13 shows a section through the tube element portion 80 of FIG. 12. The illustration according to FIG. 13 shows five such recesses 81, which are formed as slots. When the tube element portion 80 is part of a tube element 1, the inner diameter of the tube element portion 80 corresponds to the inner diameter 7 of the tube element 1, as shown in one of the foregoing embodiments.

The slots or cuts according to the embodiment shown in FIGS. 12 and 13 serve to improve the buckling stability and to increase the flexibility of the tube element portion 80. In particular, when the slots wind in the shape of a spiral, any torsional forces can be excluded. The tube element portion has a sheath 82 which is partially connected via the connecting elements 83, 84 on the one hand by the staggered arrangement of the slots to one another and on the other hand due to an inclination of the slots with respect to the longitudinal axis.

FIG. 13 shows a possible exemplary arrangement of the connecting elements 83 on the circumference of the sheath in a first cross-sectional area. The number of connecting elements 83 may differ from the number shown in the drawing. The connecting elements 83 according to the present embodiment have substantially the same segment length. The length of the segment of each of the connecting elements 83 may differ from each length of another segment of another connecting element 83. The connecting elements 83 may in particular have the same segment length. The slots extending between the connecting elements 83 may have the same slot segment length.

Figure 14:
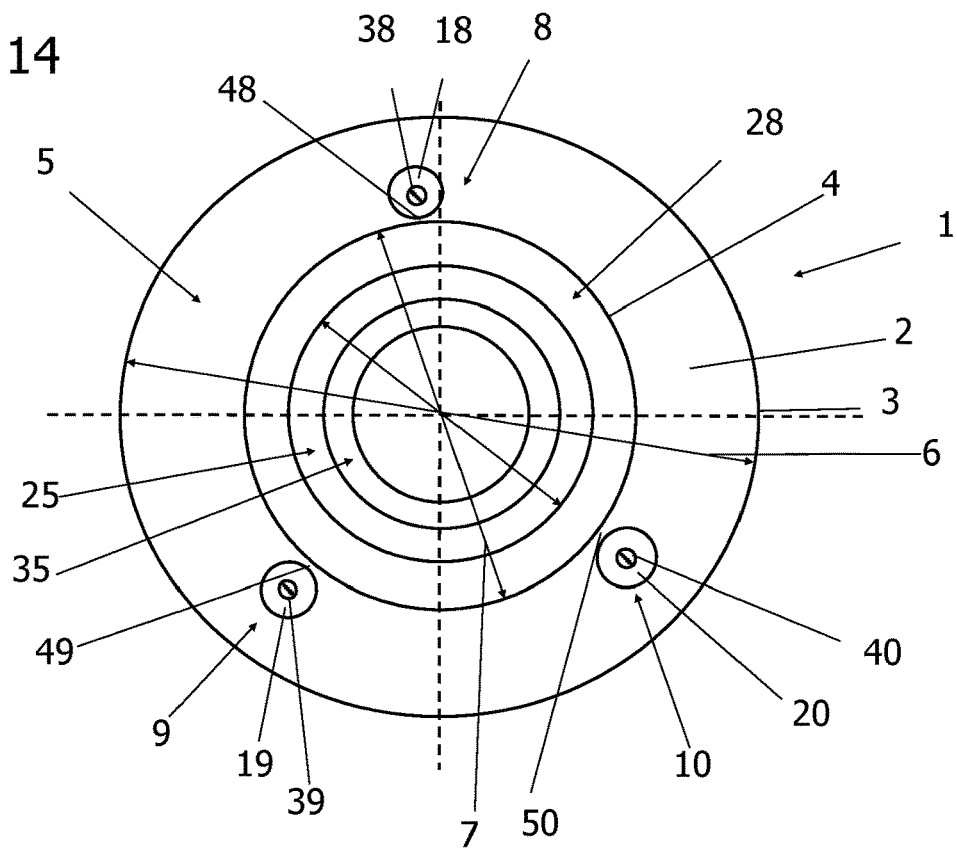

FIG. 14 shows a tube element 1 according to an eighth exemplary embodiment of a device 100 for insertion into a body passage, wherein the tube element 1 has a first tube element end 11 and a second tube element end 12, which is shown in FIG. 10. In FIG. 14, no hatchings have been made in order to increase the clarity of the representation. FIG. 14 shows a cross-sectional element 5, that is to say a radial section normal to the longitudinal axis of the tube element 1. According to this illustration, the longitudinal axis of the tube element 1 extends normal to the plane of the drawing. Between the first and second tube element ends 11, 12, a longitudinal dimension 13 is formed which coincides with the longitudinal axis if the tube element 1 has a rotationally symmetrical shape.

The tube element 1 has a sheath 2, which forms the cross-sectional element 5, which comprises an outer wall 3 and an inner wall 4. The sheath 2 has an outer diameter 6, wherein the longitudinal dimension 13 amounts to at least ten times the outer diameter 6. The inner diameter 7 of the sheath 2 corresponds to the outer diameter of an annular opening 28 which adjoins the inner wall 4. Inside the opening 28 extends an inner tube 25, which contains for example a plastic or consists of plastic. The inner tube 25 is to be regarded here as an exemplary embodiment of a tube element portion 70, which is shown in one of FIGS. 2-7, 10, 11. The outer diameter of the inner tube 25 corresponds to the inner diameter of the opening 28. Advantageously, the inner tube 25 is arranged concentrically with respect to the sheath 2.

The inner tube 25 may include a stiffening element 35 or a stiffening element 35 may be mounted on the inner side of the inner tube 25. The stiffening element 35 is to be regarded here as an exemplary embodiment of a tube element portion 80, which is shown in one of FIGS. 2-7, 10, 11. The stiffening element 35 can be configured as a spirally arranged wire element or band element. According to an embodiment, not shown, the stiffening element can be configured as a mesh. Inside the stiffening element 35 and/or the inner tube 25 there is provided a central cavity or lumen, if no stiffening element is provided or the stiffening element is arranged in the interior of the inner tube 25, which is not shown in the drawing. The inner tube 25 or the stiffening element 35 can be provided with a coating so that a liquid located in the central cavity does not undergo any interaction with the inner tube 25 or the stiffening element 35. The stiffening element 35 can be laminated, for example, in the inner tube 25. The stiffening element 35 can be located between the central cavity and the inner tube 25 or it can be located between the inner tube 25 and the cross-sectional element 5, which is not shown in the drawing.

The first tube element end 11, according to FIG. 10, has a first frontal element 14 and the second tube element end 12 has a second frontal element 15. Between the first frontal element 14 and the second frontal element 15, a cross-sectional element 5 is arranged. The cross-sectional element 5 may be located at any position between the first tube element end 11 and the second tube element end 12.

The cross-sectional element 5 contains a plurality of opening arrangements 8, 9, 10. The opening arrangements 8, 9, 10 extend in the direction of the longitudinal dimension 13 from the first frontal element 14 to the second frontal element 15 and from the first tube element end 11 to the second tube element end 12. Each of the opening arrangements 8, 9, 10 comprises a first opening 18, 19, 20 containing an insert element 38, 39, 40 and a second opening 28 whose internal pressure is adjustable by a pressure changing means. By means of the pressure changing means, an overpressure or a negative pressure can be generated in the second opening 28 relative to the internal pressure in the first opening 18, 19, 20. The tube element 1 according to this embodiment includes three opening arrangements 8, 9, 10, which is to be regarded as an exemplary embodiment only. The tube element 1 can therefore in particular contain more than three opening arrangements.

Each of the opening arrangements 8, 9, 10 has an intermediate wall 48, 49, 50, whose wall thickness is substantially smaller than the distance of the respective opening arrangement 8, 9, 10 from the outer wall 3.

The intermediate wall 48, 49, 50 is displaceable by a change in the internal pressure of one of the first or second openings 18, 19, 20, 28 such that the insert element 38, 39, 40 is in the respective first opening 18, 19, 20 selectively blockable or detachable.

Figure 15:
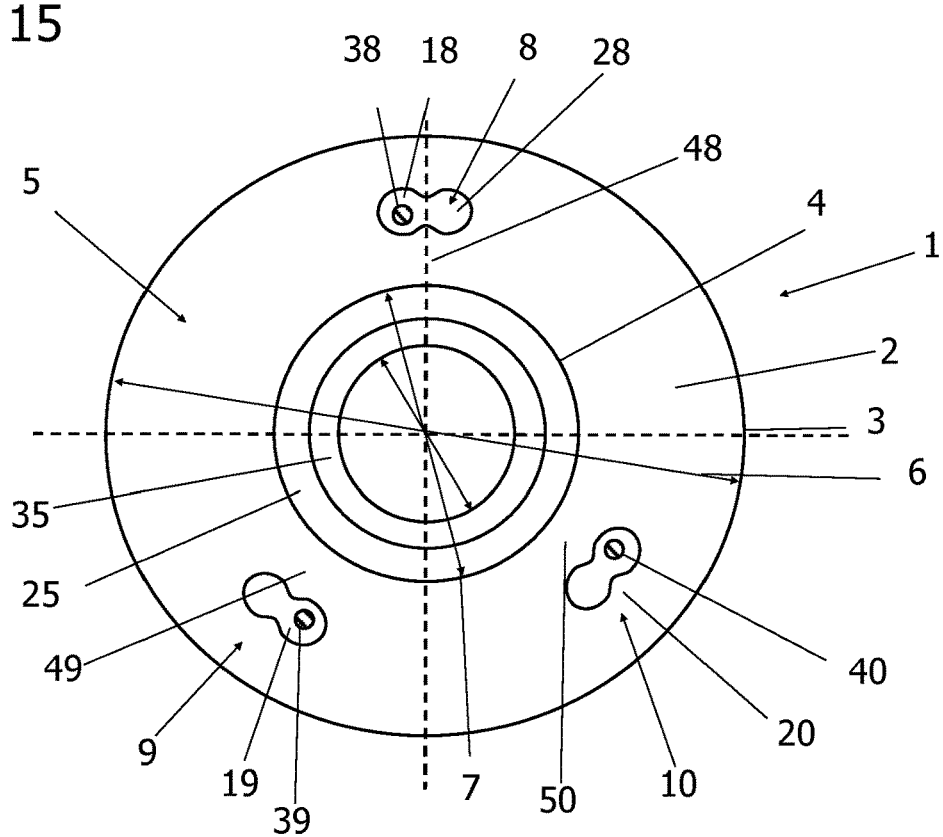

FIG. 15 shows a tube element 1 according to an ninth exemplary embodiment of a device 100 for insertion into a body passage, wherein the tube element 1 has a first tube element end 11 and a second tube element end 12, which is shown in FIG. 10. In FIG. 15, no hatchings have been made in order to increase the clarity of the representation. FIG. 15 shows a cross-sectional element 5, that is to say a radial section normal to the longitudinal axis of the tube element 1. Between the first and second tube element ends 11, 12, a longitudinal dimension 13 is formed which coincides with the longitudinal axis if the tube element 1 has a rotationally symmetrical shape. The tube element 1 has a sheath 2 which comprises an outer wall 3 and an inner wall 4. The sheath 2 has an outer diameter 6, wherein the longitudinal dimension 13 amounts to at least ten times the outer diameter 6. The inner diameter 7 of the sheath 2 corresponds to the outer diameter of an inner tube 25 which adjoins the inner wall 4. The inner tube 25 is to be regarded here as an exemplary embodiment of a tube element portion 70, which is shown in one of FIGS. 2-7, 10, 11. The inner tube 25 includes, for example, a plastic or consist of a plastic. The outer diameter of the inner tube 25 corresponds to the inner diameter 7 of the sheath. Advantageously, the inner tube 25 is arranged concentrically with respect to the sheath 2.

The inner tube 25 may include a stiffening element 35 or a stiffening element 35 may be mounted on the inner side of the inner tube 25. The stiffening element 35 is to be regarded here as an exemplary embodiment of a tube element portion 80, which is shown in one of FIGS. 2-7, 10, 11. The stiffening element 35 can be configured as a spirally arranged wire element or band element. Inside the stiffening element 35 and/or the inner tube 25 there is provided a central cavity or lumen, if no stiffening element is provided or the stiffening element is arranged in the interior of the inner tube 25, which is not shown in the drawing. The stiffening element 35 can be laminated, for example, in the inner tube 25. The stiffening element 35 can be located between the central cavity and the inner tube 25 or it can be located between the inner tube 25 and the cross-sectional element 5, which is not shown in the drawing. The inner tube 25 or the stiffening element 35 can be provided with a coating so that a liquid located in the central cavity does not undergo any interaction with the inner tube 25 or the stiffening element 35.

The first tube element end 11, according to FIG. 10, has a first frontal element 14 and the second tube element end 12 has a second frontal element 15. Between the first frontal element 14 and the second frontal element 15, a cross-sectional element 5 is arranged. The cross-sectional element 5 may be located at any position between the first tube element end 11 and the second tube element end 12.

The cross-sectional element 5 contains a plurality of opening arrangements 8, 9, 10. The opening arrangements 8, 9, 10 extend in the direction of the longitudinal dimension 13 from the first frontal element 14 to the second frontal element 15 and from the first tube element end 11 to the second tube element end 12. Each of the opening arrangements 8, 9, 10 comprises a first opening 18, 19, 20 containing an insert element 38, 39, 40 and a second opening 28, 29, 30 whose internal pressure is adjustable by a pressure changing means. By means of the pressure changing means, an overpressure or a negative pressure can be generated in the second opening 28, 29, 30 and/or in the first opening 18, 19, 20. The tube element 1 according to this embodiment includes three opening arrangements 8, 9, 10. The first openings 18, 19, 20 may be connected to the corresponding second openings 28, 29, 30 via a channel or a constriction. Optionally, a partition may be provided as in one of the embodiments according to FIGS. 1-6. The partition may also be formed as a film or membrane, which is not shown in the drawing.

By a change in the internal pressure in each one of the first or second openings 18, 19, 20, 28, 29, 30 whose opening walls are displaceable so that the insert element 38, 39, 40 in the first opening 18, 19, 20 is either blockable or is releasable. In particular, one of the first or second openings 18, 19, 20, 28, 29, 30 can be evacuated so that the opening walls come into contact with the insert element 38, 39, 40. Alternatively, each one of the first or second openings 18, 19, 20, 28, 29, 30 are subjected to an overpressure, whereby the position of the insert element 38, 39, 40 in the associated opening 18, 19, 20 can be fixed.

The tube element according to one of the preceding embodiments can be configured as a composite element containing at least two different materials.

It should be apparent to those skilled in the art that many more modifications besides those already described are possible without departing from the inventive concepts herein. Of course, it is possible, in particular, to combine any the shapes of the openings and the opening arrangements of the embodiments arbitrarily with one another in order to obtain optimal properties of the tube element for the corresponding application. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of an element or compound selected from the group consisting of A, B, C . . . and N, the text should be interpreted as requiring only one element from the group, not A plus N, or B plus N, etc.

The invention claimed is:

1. A tube element for a device for introduction into a body passage wherein the tube element comprises a first tube element end and a second tube element end, wherein a longitudinal dimension is formed between the first tube element end and the second tube element end, wherein the tube element has a sheath comprising an outer wall and an inner wall, wherein the sheath has an external diameter, wherein the longitudinal dimension amounts to at least ten times the external diameter, wherein a cross-sectional element of the sheath is arranged between the first tube element end and the second tube element end, wherein the cross-sectional element contains a plurality of opening arrangements, wherein the plurality of the opening arrangements extend along the longitudinal dimension from the first tube element end to the second tube element end, wherein each one of the plurality of the opening arrangements comprises a first opening containing an insert element and a second opening, wherein the second opening is of a cross-section which is configured as an annular opening, wherein an internal pressure of which can be changed by a pressure changing means, wherein the pressure changing means comprises a pressure source or a vacuum source, wherein each of the plurality of the opening arrangements has an intermediate wall, and wherein at least one of the plurality of the opening arrangements has a first intermediate wall, located between the first opening and the second opening, the first intermediate wall comprises a wall thickness that is smaller than a distance of the at least one opening arrangements from the outer wall or the inner wall.

2. The tube element of claim 1, wherein by means of the pressure changing means, an overpressure or a negative pressure can be generated in the second opening relative to an internal pressure in the first opening.

3. The tube element of claim 1, wherein the intermediate wall is displaceable by a change in the internal pressure of one of the first or second openings such that the insert element in the first opening is selectively blockable or detachable.

4. The tube element of claim 1, which contains at least three opening arrangements.

5. The tube element of claim 1, which consists of a plurality of tube element portions.

6. The tube element of claim 5, wherein the tube element portion has at least one recess in the sheath.

7. The tube element of claim 6, wherein a wall thickness of the tube element portion in the region of the recess is smaller than a wall thickness of the sheath.

8. The tube element of claim 7, wherein the recess is configured as a slot.

9. The tube element of claim 1, which is formed as a composite element containing at least two different materials.

10. The tube element of claim 9, wherein the sheath is formed as a composite element which contains at least two different materials.

11. The tube element of claim 5 wherein a tube element portion extends adjacently to the inner wall of the sheath, which is designed as an inner tube or as a stiffening element.

12. The tube element of claim 11, wherein the inner tube contains a plastic material or consists of a plastic material.

13. The tube element of claim 11, wherein the inner tube includes a stiffening element or a stiffening element is arranged on the inside of the inner tube.

14. The tube element of claim 13, wherein the stiffening element is configured as a spirally arranged wire element or a band element or as a mesh.

15. The tube element of claim 1, wherein the tube element contains a central cavity for receiving a fluid.

16. The tube element of claim 15, wherein the outer wall of the cavity is formed by the inner wall of the sheath or the tube element comprising a plurality of tube element portions.

17. The tube element of claim 15, wherein the outer wall of the cavity is formed by the inner wall of the inner tube or the stiffening element.

18. The tube element of claim 15, wherein one of the inner wall of the sheath, the tube element portions, the inner tube or the stiffening element contains a coating.

* * * * *